(12) United States Patent
Schleep et al.

(10) Patent No.: US 7,586,004 B2
(45) Date of Patent: Sep. 8, 2009

(54) METHOD FOR CONTINUOUSLY PRODUCING ALKYLAMINO(METH)ACRYLAMIDES

(75) Inventors: Volker Schleep, Einhausen (DE); Thomas Mertz, Bensheim (DE)

(73) Assignee: Roehm GmbH & Co. KG, Darmstadt (DE)

( * ) Notice: Subject to any disclaimer, the term of this patent is extended or adjusted under 35 U.S.C. 154(b) by 258 days.

(21) Appl. No.: 10/556,798

(22) PCT Filed: Apr. 13, 2004

(86) PCT No.: PCT/EP2004/003862

§ 371 (c)(1),
(2), (4) Date: Dec. 1, 2006

(87) PCT Pub. No.: WO2004/103952

PCT Pub. Date: Dec. 2, 2004

(65) Prior Publication Data

US 2007/0149811 A1   Jun. 28, 2007

(30) Foreign Application Priority Data

May 22, 2003   (DE) .................... 103 23 699

(51) Int. Cl.
*C07C 231/00* (2006.01)

(52) U.S. Cl. .............. 564/134; 564/135; 564/137; 564/138; 564/139; 564/141

(58) Field of Classification Search ............... 564/134, 564/135, 137, 138, 141, 139
See application file for complete search history.

(56) References Cited

U.S. PATENT DOCUMENTS 4,675,442 A * 6/1987 Besecke et al. ............. 564/135

FOREIGN PATENT DOCUMENTS

| | | |
|---|---|---|
| DE | 40 27 843 | 3/1992 |
| EP | 0 362 119 | 4/1990 |

* cited by examiner

*Primary Examiner*—Taylor Victor Oh
(74) *Attorney, Agent, or Firm*—Oblon, Spivak, McClelland, Maier & Neustadt, P.C.

(57) ABSTRACT

The invention relates to a process for continuously preparing alkylamino(meth)acrylamide by reacting methyl (meth)acrylate, ethyl (meth)acrylate or amines having a high boiling point compared to methanol or ethanol. A special workup technique which includes removing water from the amine before entering the reactor allows product qualities which have hitherto not been attained to be achieved. In addition, very high space-time and overall yields can be achieved.

19 Claims, 1 Drawing Sheet

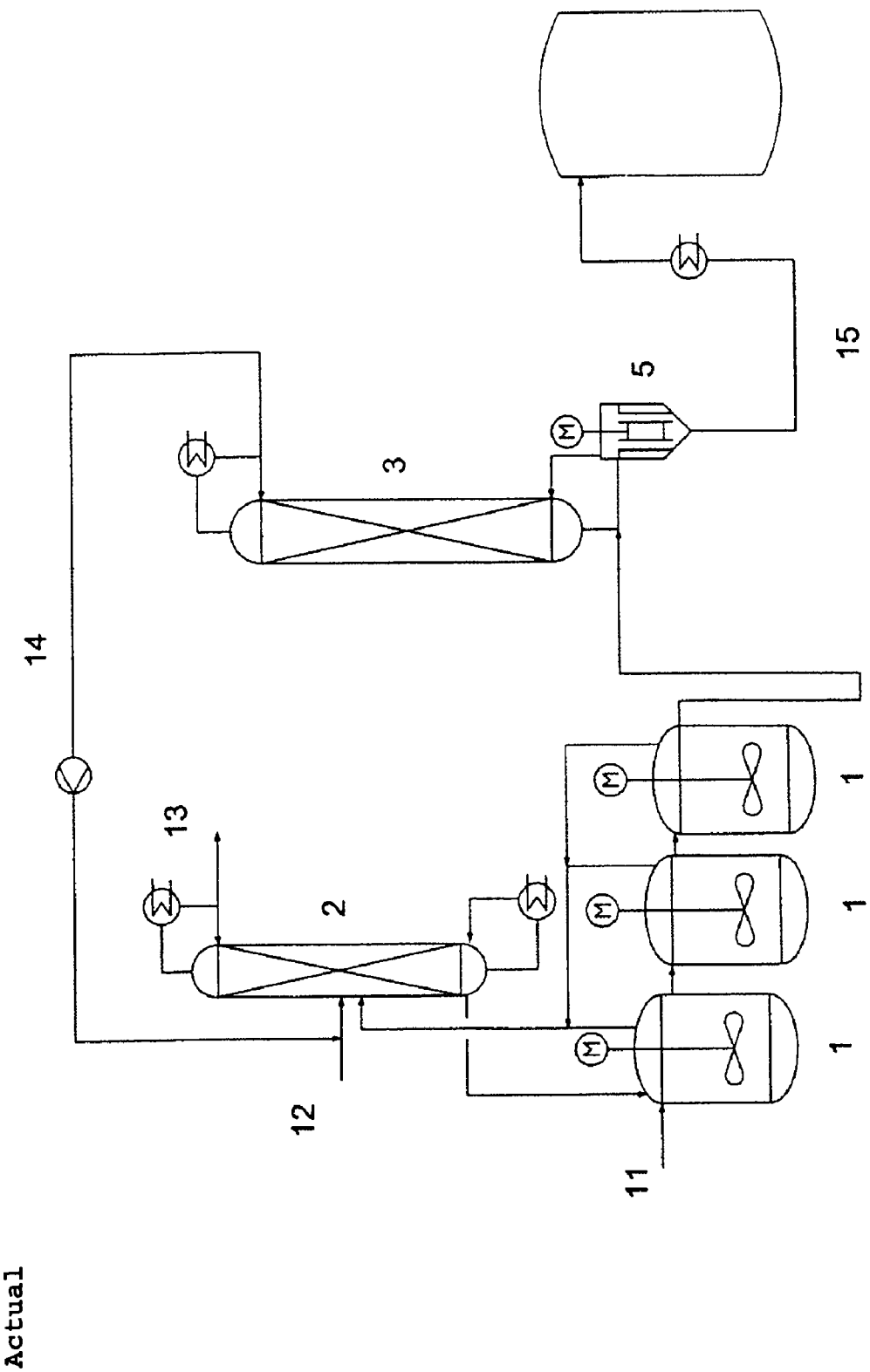

METHOD FOR CONTINUOUSLY PRODUCING ALKYLAMINO(METH)ACRYLAMIDES

BACKGROUND OF THE INVENTION

1. Field of the Invention

The invention relates to a further continuous process for preparing alkylamino(meth)acrylamides (C) by continuously aminolysing, for example, methyl (meth)acrylate (A) with amines (B) to release methanol (D) by the following reaction equation:

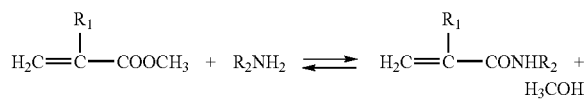

where:

$R^1$=hydrogen or methyl $R^2$ is a linear, branched or cyclic alkyl radical, an aryl radical which may also be substituted by one or more alkyl groups; the linear, cyclic or branched alkyl radical may have a length of 2-12 carbon atoms, for example ethyl, propyl, isopropyl, butyl, isobutyl, tert-butyl, pentyl, hexyl, heptyl, octyl, isooctyl, nonyl, decyl, undecyl, and may optionally be mono- or polysubstituted by $NR^3R^4$ or $OR^5$;

either $R^3$ or $R^4$ may assume the definition of hydrogen, and in addition:

$R^1$, $R^4$ and $R^5$ may be either the same or different and be an alkyl group having 1-12 carbon atoms, for example methyl, ethyl, propyl, isopropyl, butyl, isobutyl, tert-butyl, pentyl, hexyl, heptyl, octyl, isooctyl, nonyl, decyl, undecyl or hydrogen.

$R^2$ may also be $[(R^6\text{-}O)_n]\text{-}R^7$ where:

$R^6$ may be a $C_1$-$C_4$-alkyl group which may also be branched, for example methyl, ethyl, propyl, isopropyl, butyl, isobutyl or tert-butyl.

Alkylamido (meth)acrylates m: 1-4

$R^7$ may be the methyl group or the ethyl group.

Useful amines include the following compounds: Dimethylaminoethylamine, diethylaminoethylamine, dipropylaminoethylamine, diisopropylaminoethylamine, dibutylaminoethylamine, diisobutylaminoethylamine, dimethylaminopropylamine, diethylaminopropylamine, dipropylaminopropylamine, diisopropylaminopropylamine, dibutylaminopropylamine, diisobutylaminopropylamine, dimethylaminobutylamine, diethylaminobutylamine, dipropylaminobutylamine, diisopropylaminobutylamine, dibutylaminobutylamine, diisobutylaminobutylamine, methylamine, cyclohexylamine, dimethylaminohexylamine, diethylaminohexylamine.

Particular preference is given, in addition to dimethylaminopropylamine, to dimethylaminoethylamine, dimethylaminobutylamine, dimethylaminopentylamine and dimethylaminohexylamine.

2. Prior Art

The literature describes many batchwise transesterification processes (batch transesterification processes) in conjunction with different catalysts.

The search for economically more viable processes led to the discovery of continuous transesterification processes in which the reactants are fed continuously and the products are removed continuously. The continuous transesterification processes have the following advantages over the batchwise transesterification processes: the process can be more easily automated and can be operated with a reduced need for personnel, the product quality has better reproducibility and less variability, the plant capacity increases as a consequence of the absence of the sequential working through of the individual preparation steps (filling, reaction, low boiler removal, product removal, emptying). The process has a higher space-time yield than a batch process.

Continuous transesterification processes are known.

EP 0 960 877 (Elf Atochem S.A.) describes a continuous process for preparing methacrylate esters of dialkylaminoalcohols. Dialkylaminoalcohols are reacted generally with methyl (meth)acrylate to obtain dialkylaminoalkyl(meth)acrylate by the following process:

The mixture of the starting materials (methyl (meth)acrylate and dialkylaminoalcohol) is fed continuously together with a tetraalkyl titanate as a transesterification catalyst (for example tetrabutyl, tetraethyl or tetra(2-ethylhexyl)titanate) and at least one polymerization inhibitor (for example phenothiazine, tert-butylcatechol, hydroquinone monomethyl ether or hydroquinone) to a tubular reactor where the conversion is effected at a temperature of 90-120° C. to the dialkylamino (meth)acrylate while simultaneously continuously removing the azeotropic methyl (meth)acrylate/methanol mixture. The crude reaction mixture (crude ester) is fed to a first distillation column in which a substantially catalyst-free stream is removed under reduced pressure at the top of the distillation column, and the catalyst and also a little dialkylaminoalkyl(meth)acrylate are removed in the bottom of the distillation column. The top stream of the first distillation column is then fed to a second distillation column in which a stream of low-boiling products having a little dialkylaminoalkyl(meth)acrylate is removed under reduced pressure at the top and a stream consisting of mainly dialkylaminoalkyl (meth)acrylate and also polymerization inhibitor(s) is removed at the bottom and fed to a third distillation column. In the third distillation column, a rectification is carried out under reduced pressure in which the desired pure dialkylaminoalkyl (meth)acrylate ester is removed at the top and essentially the polymerization inhibitor or the polymerization inhibitors are removed at the bottom. The bottom stream of the first distillation column is recycled into the reactor after further purification with the aid of a film evaporator, just like the top stream from the second distillation column.

This process dispenses with dewatering of the alcohols before use, which may lead to increased deactivation of the tetraalkyl titanate used as a consequence of hydrolysis up to the formation of undesired solid deposits. In addition, the process has the disadvantage that the catalyst is thermally stressed at relatively high temperatures in the bottom of the first distillation column. This can easily lead to decomposition of the catalyst.

In this process, both the unconverted reactants and the product are rectified via the top twice altogether. This entails very high energy costs and a total of 4 rectification columns, some of which have to have very large dimensions. The process is therefore burdened with very high capital and operating costs.

EP 0 968 995 (Mitsubishi Gas Chemical Comp.) describes a continuous process for preparing alkyl(meth)acrylates using a reaction column. The transesterification reaction is effected directly in a distillation column (i.e. reactor and distillation column for removing the methyl (meth)acrylate/methanol azeotrope form one apparatus), to which the starting materials (methyl (meth)acrylate and alcohol) are fed continuously. The catalyst required, here likewise preferably a titanium compound, is disposed in the distillation column. In the case of a homogeneous catalyst, the catalyst is metered continuously into the distillation column. However, as a consequence of the flushing effect by the liquid reflux in the distillation column, the use of homogeneous catalysts in a distillation column leads to increased catalyst demand, and, when a solid catalyst precipitate occurs, to fouling of the column internals. In the case of a heterogeneous catalyst, the catalyst is disposed in the reaction column. However, the positioning of the catalyst in the distillation column is disadvantageous, because an increased pressure drop then occurs in the distillation column and very high cost and inconvenience is additionally associated with the regular cleaning of the distillation column. In addition, heterogeneous catalysts may deactivate for example as a consequence of undesired polymerization.

DE 4 027 843 (Röhm GmbH) describes a continuous process for preparing N-substituted (meth)acrylamides by transesterifying alkyl esters of (meth)acrylic acid with aliphatic and aromatic amines. The reaction temperature is >150°, the pressure approx. 160 bar. There is no catalyst.

SUMMARY OF THE INVENTION

It is an object of the present invention to provide a continuous process for aminolysing methyl (meth)acrylate with amines having high boiling points, compared to methanol, which avoids the disadvantages of the two above-described processes. (Meth)acrylic esters or alkyl(meth)acrylates refer hereinbelow to esters and derivatives of acrylic acid and of methacrylic acid, for example methyl methacrylate or ethyl methacrylate. In addition, the novel process should make available a product of better quality than those hitherto on the market. A better quality refers to a lower crosslinker content or a lower content of addition products of the amines to the double bond of the starting ester or to the double bond of the product ester. A crosslinker which may be formed is alkylmethacrylamide. In addition, amino(meth)acrylates should be prepared by the novel process at very low cost and inconvenience and energetically more favourably (i.e. less expensively). The personnel demands for operating the plant should be reduced.

This object, and also other objects which are not specifically detailed but can be immediately discerned or derived from the introductory discussion of the prior art are achieved by a process having the features described in the claims. Advantageous modifications of the process according to the invention are protected in the claims.

BRIEF DESCRIPTION OF THE DRAWINGS

The FIGURE schematically illustrates the process of the invention.

In the FIGURE the reference numerals represent the following as described in the

| | |
|---|---|
| 1. | At least one reactor |
| 2. | Azeotrope distillation column |
| 3. | Low boiler distillation column |
| 5. | Gentle Film evaporator |
| 6. | Purifying Distillation Column |
| 11. | Methyl (meth)acrylate and catalyst feed |
| 12. | Amine feed |
| 13. | Methanol/methyl (meth)acrylate azeotrope |
| 14. | Low boiler recycle stream |
| 15. | Crude product |

The reactant, methyl (meth)acrylate (MMA, 11), is fed continuously to a suitable reaction apparatus (1), and either a single reaction vessel or a battery of a plurality of reaction vessels connected in series may be used. It is sensible that all reaction vessels have a vapour takeoff to the azeotrope distillation column (2) to remove the methanol released in the reaction.

The amine (12) is fed continuously to the azeotrope distillation of the column for dewatering.

The tetraalkoxy titanate required as a catalyst (the tetraalkoxy titanate content based on MMA used is preferably 0.2-4% by weight), like the polymerization inhibitor or inhibitors, is likewise preferably metered continuously into the reaction apparatus (1). However, useful transesterification catalysts may also be all of the transesterification catalysts known from the prior art. Useful catalysts are, for example, zirconium acetylacetonate and further 1,3-diketonates of zirconium; mixtures of alkali metal cyanates or alkali metal thiocyanates and alkali metal halides may also be used; and also zinc compounds, for example dioctylzinc oxide, alkaline earth metal oxides or alkaline earth metal hydroxides, for example $CaO$, $Ca(OH)_2$, $MgO$, $Mg(OH)_2$, or mixtures of the aforementioned compounds, and also alkali metal hydroxides, alkali metal alkoxides and lithium chloride and lithium hydroxide; mixtures of the aforementioned compounds with the aforementioned alkaline earth metal compounds and the Li salts may also be used; dialkyltin oxides, for example dioctyltin oxide, alkali metal carbonates, alkali metal carbonates together with quaternary ammonium salts, for example tetrabutylammonium hydroxide or hexadecyltrimethylammonium bromide, and also mixed catalysts of diorganyltin oxide and organyltin halide, acidic ion exchangers, phosphorus-molybdenum heteropolyacids, titanium alkoxides, for example isopropyl titanate, chelate compounds of the metals titanium, zirconium, iron or zinc with 1,3-dicarbonyl compounds, lead compounds, for example lead oxides, lead hydroxides, lead alkoxides, lead carbonates or lead salts of carboxylic acids. Particular preference is given to a catalyst mixture of dialkyltin oxide and alkyl titanate, for example dioctyltin oxide and isopropyl titanate in a ratio of approx. 1:1 (% by wt.% by wt.). The catalyst mixture is used in amounts of 0.1-10 mass %, based on the amine used.

Useful polymerization inhibitors are, for example, hydroquinone, 4-hydroxy-2,2,6,6-tetramethylpiperidinooxyl or else bis(2-methoxycarbonylpropyl) sulphide. Hydroquinone monomethyl ether in conjunction with oxygen in question.

The amine used may contain water. The amount of water in the amine used in the case of amine is between 50 and 500 ppm (0.05-0.005% by weight). The amine is dewatered by distillation before entry into the reaction apparatus, preferably using the azeotrope column (2). In this column, the water present in the amine is removed via the top. To prevent contamination of the methanol/MMA azeotrope (13) with the amine used, the amine is preferably introduced in the lower section of the distillation column (2). The amine used may also be dewatered in other ways:

- by an upstream dewatering distillation column
or
- by treating with a dewatering agent, for example a molecular sieve,
or
- by a membrane separation process, for example a pervaporation.

The dewatering is significant since the water present in the amine may lead to irreversible damage to the catalyst (for example tetraalkyl titanate) in the reactor. The water present in the amine leads to the formation of by-products and is therefore to be strictly prevented. This dewatering step prevents the hydrolysis of the catalyst and the associated costs as a result of increased catalyst use amounts and as a result of problems with solid deposits. In addition, the purity of the product is increased by a reduced proportion of by-products.

The reaction is effected in a reaction apparatus (1) at a temperature in the range between 80 and 160° C. Preference is given to the temperature range between 110 and 135° C. To increase the reaction rate, the methanol released in the reaction is removed from the reaction mixture as an azeotrope with MMA (13) via the distillation column (2). The reaction mixture, which consists for the most part of the alkyl(meth) acrylate amide product, unconverted MMA and amine, and also small amounts of methanol, the catalyst, the polymerization inhibitors and a very small fraction of by-products, is fed after approx. 0.5-3 hours of reactor residence time (preference is given to a residence time of 0.75-1.5 hours) to a continuous falling-film evaporator (5). The vapours of the falling-film evaporator (5) are fed to a low boiler distillation column (3). The components having a low boiling point relative to the product ester, predominantly methanol, MMA and unconverted amine reactant, are removed there under reduced pressure, preferably in the range of 10-500 mbar. These are removed via the top of the distillation column and recycled (14) into the reactor region or into the azeotrope column (2). This recycle stream guarantees that there is virtually complete conversion with regard to the MMA and amine reactants based on the entire process.

The crude amide (15) which is still contaminated with catalyst, polymerization inhibitor and high-boiling by-products and occurs in the effluent of the falling-film evaporator (5) preferably contains >93% by weight of product amide and is fed for workup to a further vacuum distillation stage which works in the preferred pressure range between 20 and 200 mbar. The highly pure product amide is removed here by distillation as the top product.

The by-products formed in the process are high-boiling components relative to the reactant amine and the methyl methacrylate and therefore get into the product ester as an impurity, which distinctly reduces the product quality. This problem can be solved by using an apparatus having gentle film evaporation (5) to remove the product amine from the catalyst and the polymerization inhibitors, and also the high-boiling by-products. Suitable apparatus for this purpose is falling-film, thin-layer and short-path evaporators.

Downstream of the preparation of the alkylamino(meth) acrylamides may optionally be disposed a purifying distillation plant which may also be operated under reduced pressure, for example at 500-50 mbar.

The process according to the invention is illustrated in detail by the examples which follow, without being restricted thereto.

EXAMPLE

Continuously Described Aminolysis to Aminoesters

For continuously described preparation of N-dimethylaminopropylmethacrylamide (aminoester), 235 kg/h of MMA/catalyst feed having a proportion of 3.8% by weight of isopropyl titanate and 3.0% by weight of dioctyltin oxide of the azeotrope distillation column and 244 kg/h of N-dimethylaminopropylamine (DMAPA) are metered into the $1^{st}$ reaction vessel. In addition, the recycle stream from the top of the low boiler distillation column flowed continuously via the azeotrope column to the $1^{st}$ reaction vessel (195 kg/h having the composition 78.9% by weight of MMA, 2.12% by weight of methanol, 10.1% by weight of DMAPA and 8.88% by weight of by-products). The molar MMA:DMAPA ratio in the reactor feed was 1.23:1. In addition, the vapours of the stirred tank which had been freed of methanol in the azeotrope column were fed to the $1^{st}$ reaction vessel via the azeotrope column bottom. Under these reaction conditions, a reaction temperature of 107° C. was established in the $1^{st}$ reaction vessel. The distillate takeoff of the azeotrope column was 117 kg/h comprising 56.54% by weight of methanol, 39.12% by weight of MMA, 4.02% by weight of isopropanol and 0.5% by weight of by-products.

The effluent of the $1^{st}$ reaction vessel flowed into the $2^{nd}$ reaction vessel and the effluent of the $2^{nd}$ reaction vessel flowed into the $3^{rd}$ reaction vessel. A residence time of approx. 15 min in the $1^{st}$ reaction vessel, approx. 30 min in the $2^{nd}$ reaction vessel and approx. 60 min in the $3^{rd}$ reaction vessel resulted in the following compositions in the reactors.

| | T(° C.) | MMA (%) by wt. | DMAPA (%) by wt. | Amino ester (%) by wt. | Methanol (%) by wt. | By-products (%) by wt. |
|---|---|---|---|---|---|---|
| $1^{st}$ reactor | 107 | 62.7 | 10.23 | 22.07 | 0.62 | 4.38 |
| $2^{nd}$ reactor | 111 | 55.6 | 10.15 | 27.69 | 0.59 | 5.97 |
| $3^{rd}$ reactor | 130 | 46.8 | 4.86 | 41.29 | 1.24 | 5.81 |

The vapours of the individual reaction vessels were fed continuously to the azeotrope column.

The effluent of the $3^{rd}$ reaction vessel flowed continuously to the thin-film evaporator of a low boiler column in which unconverted DMAPA, MMA and methanol were removed as distillate (195 kg/h) and fed back to the $1^{st}$ reaction vessel as recycle stream. The bottom attempt of the thin-film evaporator of the low-boiler column was 426 kg/h and had the composition: 93% of amino ester product, 0.5% of DMAPA, 0.2% of MMA, 2.15% by weight of an MMA-amine adduct and 4.25% by weight of other by-products.

The invention claimed is:
1. A continuous process of high catalyst efficiency and product purity for the preparation of an alkylamino(meth) acrylamide of formula (C) in a suitable reaction apparatus,

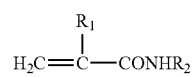

(C)

where $R_1$ is an H or $CH_3$ group and $R_2$ is a linear, branched or cyclic alkyl radical or aryl radical having 2 to 12 carbon atoms, the process comprising:

continuously feeding to the suitable reaction apparatus:

an amine of formula (B):

a compound of formula (A):

wherein $R^3$ is methyl or ethyl,
a transesterification catalyst, and
at least one polymerization inhibitor;
removing water from the amine of formula (B);
reacting the amine of formula (B) from which the water was removed, with the compound of formula (A) to form a reaction mixture comprising the alkylamino(meth)acrylamide of formula (C);
continuously removing an azeotropic mixture comprising an alcohol of formula (D):

and the compound of formula (A) to an azeotropic distillation column;
continuously conducting the reaction mixture out of the at least one reactor to a gentle film evaporator; and
purifying a bottom stream from the gentle film evaporator in a purifying distillation column;
wherein
in the continuous feeding, the amine of formula (B) is fed to the at least one reactor via the azeotropic distillation column, and
the suitable reaction apparatus comprises:
at least one reactor,
an azeotropic distillation column connected to the at least one reactor,
a gentle film evaporator connected to the at least one reactor,
a low boiler distillation column connected to the falling film evaporator at a lower position of the low boiler distillation column and connected to the azeotropic distillation column at an upper position of the low boiler distillation column, and
a purifying distillation column connected to the falling film evaporator.

2. The process according to claim 1, wherein
a stream of the gentle film evaporator is fed continuously to a purifying distillation column in which the highly pure product amide of the formula (C) is removed via the top by distillation under reduced pressure, and the catalyst and the polymerization inhibitors, and also the high-boiling by-products with a small portion of product amide of the formula (C) are removed via the bottom.

3. The process according to claim 1, wherein
the amine of formula (B) is dewatered in the azeotropic distillation column connected to the at least one reactor.

4. The process according to claim 1, wherein
a molar ratio of the compound of formula (A) to the amine of formula (B) in the feed to the reactor is between 1 and 2.

5. The process according to claim 1, wherein
the transesterification catalyst is a tetraalkyl titanate.

6. The process according to claim 1, wherein
an amount of transesterification catalyst is 0.1-10% by weight, based on an amount of the compound of formula (A).

7. The process according to claim 6, wherein
the amount of transesterification catalyst is 0.2-7% by weight.

8. The process according to claim 1, wherein
the transesterification catalyst is a mixture of dioctyltin oxide and isopropyl titanate in a ratio of 1:1 in % by weight.

9. The process according to claim 8, wherein
an amount of the transesterification catalyst mixture is 0.1-10% by weight, based on the amount of the compound of formula (A).

10. The process according to claim 2, wherein
the amount of the transesterification catalyst mixture is 0.2-7% by weight.

11. The process according to claim 1, wherein
the polymerization inhibitor is at least one selected from the group consisting of phenothiazine, tert-butylcatechol, hydroquinone monomethyl ether, hydroquinone and mixtures thereof, and an amount of the polymerization inhibitor is between 100 and 5000 ppm, based on the weight of the reaction mixture.

12. The process according to claim 1, wherein
the polymerization inhibitor comprises oxygen.

13. The process according to claim 1, wherein
the amine of formula (B) is dimethylaminopropylamine.

14. The process according to claim 1, wherein
a pressure in the low boiler distillation column is between 20 and 500 mbar.

15. The process according to claim 1, wherein
a residence time of the reaction mixture in the suitable reaction apparatus is between 0.5 and 1.5 hours.

16. The process according to claim 4,
wherein
the molar ratio of the compound of formula (A) to the amine of formula (B) in the feed to the reactor is in the range from 1.05 to 1.15.

17. The process according to claim 2, wherein a pressure within the purifying distillation column is in the range from 20 to 200 mbar.

18. The process according to claim 2, wherein the gentle film evaporator is an evaporator selected from the group consisting of a falling film evaporator, a thin-layer evaporator and a short-path evaporator.

19. The process according to claim 18, wherein the gentle film evaporator is a falling film evaporator.

* * * * *